United States Patent
Matsui et al.

(10) Patent No.: US 11,656,219 B2
(45) Date of Patent: May 23, 2023

(54) APPARATUS AND METHOD FOR STORING THIN FILM DEVICE AND METHOD FOR MEASURING BIOLOGICAL MOLECULE

(71) Applicant: HITACHI HIGH-TECHNOLOGIES CORPORATION, Tokyo (JP)

(72) Inventors: Kazuma Matsui, Tokyo (JP); Michiru Fujioka, Tokyo (JP); Yusuke Goto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 637 days.

(21) Appl. No.: 16/624,265

(22) PCT Filed: Jul. 7, 2017

(86) PCT No.: PCT/JP2017/024927
§ 371 (c)(1),
(2) Date: Dec. 18, 2019

(87) PCT Pub. No.: WO2019/008736
PCT Pub. Date: Jan. 10, 2019

(65) Prior Publication Data
US 2020/0116697 A1   Apr. 16, 2020

(51) Int. Cl.
G01N 33/487 (2006.01)
C12Q 1/6869 (2018.01)
B82Y 5/00 (2011.01)

(52) U.S. Cl.
CPC ..... *G01N 33/48721* (2013.01); *C12Q 1/6869* (2013.01); *G01N 33/48785* (2013.01); *B82Y 5/00* (2013.01); *C12Q 2565/631* (2013.01)

(58) Field of Classification Search
CPC ....... G01N 33/48721; G01N 33/48785; G01N 27/00; G01N 33/483; C12Q 1/6869; C12Q 2565/631; C12Q 1/68; C12Q 2527/125; C12Q 2565/607; B82Y 5/00; C12M 1/00; C12N 15/00
See application file for complete search history.

(56) References Cited

U.S. PATENT DOCUMENTS

| | | | |
|---|---|---|---|
| 2011/0308950 A1 | 12/2011 | Sakai et al. | |
| 2015/0060277 A1* | 3/2015 | Golovchenko | B01L 3/50273 204/453 |
| 2016/0153960 A1 | 6/2016 | Kato et al. | |
| 2018/0313813 A1 | 11/2018 | Fujioka et al. | |
| 2018/0335417 A1 | 11/2018 | Goto et al. | |

FOREIGN PATENT DOCUMENTS

| | | |
|---|---|---|
| EP | 1548444 A1 | 6/2005 |
| JP | 2017-116379 A | 6/2017 |
| WO | 2010/116595 A1 | 10/2010 |
| WO | 2014/208184 A1 | 12/2014 |
| WO | 2017/090087 A1 | 6/2017 |
| WO | 2017/110226 A1 | 6/2017 |

OTHER PUBLICATIONS

Kowalczyk et al, Slowing down DNA Translocation through a Nanopore in Lithium Chloride, 2012, Nano Lett., 12, 1038-1044. (Year: 2012).*
Zhao et al, Monolithically integrated PCR biochip for DNA amplification, 2003, 108, 162-167. (Year: 2003).*
Venta, K., et al., "Differentiation of Short, Single-Stranded DNA Homopolymers in Solid-State nanopores", ACS Nano, 2013; 7 (5), pp. 4629-4636.
Yanagi, I., et al., "Fabricating nanopores with diameters of sub-1 nm to 3 nm using multilevel pulse-voltage injection", Scientific Reports, 2014, pp. 1-7; 4 (5000).
International Search Report and Written Opinion for related International Application No. PCT/JP2017/024927, dated Sep. 19, 2017; English translation of ISR provided; 6 pages.
Office Action for related Great Britain Patent Application No. 1917971.2, dated Nov. 19, 2020 (5 pages).

* cited by examiner

*Primary Examiner* — Narayan K Bhat
(74) *Attorney, Agent, or Firm* — Procopio, Cory, Hargreaves & Savitch LLP

(57) ABSTRACT

An apparatus for storing a thin film device, the apparatus including: a thin film device 3 having an insulating thin film containing Si and having a thickness of 100 nm or less; a solution in contact with the thin film; and a container having a tank that seals the solution, wherein the solution is a solution that satisfies any of the following conditions (1) to (3).

(1) A solution containing water in a volume ratio of 0% or more to 30% or less
(2) A solution cooled and maintained at a temperature equal to or higher than a solidification point and lower than 15° C.
(3) A solution that contains a salt with a concentration of 1 mol/L or more and a saturation concentration or less and is cooled and maintained to a temperature equal to or higher than a solidification point and lower than 25° C.

6 Claims, 14 Drawing Sheets

(A)

(B)

(C)

(A)

(B)

(C)

(A)

△ PURE WATER (25°C)
◆ PURE WATER (40°C)
× PURE WATER (60°C)
○ PURE WATER (80°C)

(B)

APPARATUS AND METHOD FOR STORING THIN FILM DEVICE AND METHOD FOR MEASURING BIOLOGICAL MOLECULE

CROSS-REFERENCE TO RELATED APPLICATIONS

This application is a U.S. National Stage entry of PCT Application No: PCT/JP2017/024927 filed Jul. 7, 2017, the contents of which are incorporated herein by reference.

TECHNICAL FIELD

The present invention relates to an apparatus and a method for storing a thin film device used in a current measurement device that measures an ionic current when a subject passes through a nanopore and relates to a method for measuring a biological molecule.

BACKGROUND ART

In the field of next-generation DNA sequencers, nanopore sequencers have attracted attention as a method for electrically and directly measuring DNA base sequences without performing an extension reaction or fluorescent labels. A nanopore device used in a nanopore sequencer has a thin film in which a nanopore is embedded. A solution is disposed on both sides of the thin film, and the solution communicates through the nanopore. In this state, when a voltage is applied to the nanopore via the solution, an ionic current passing through the nanopore flows. When DNA passes through the nanopore, the nanopore is blocked differently depending on a difference between bases constituting a DNA so that a difference between current values is generated, and thus, a base sequence can be determined.

There are mainly two types of nanopore sequencing methods, that is, a bio-nanopore method and a solid-state nanopore method, depending on the material constituting the nanopore. The bio-nanopore method uses a pore of a modified protein (*Mycobacterium smegmatis* porin A (MspA) or the like) embedded in a lipid bilayer as a detecting part, and the solid-state nanopore method uses a pore processed into an inorganic material as a detecting part. As compared with the bio-nanopore method, the solid-state nanopore method has less reagent dependency and fewer pretreatment processes, and attracts attention as a method capable of reading at low cost.

There are mainly two types as a method for producing a solid-state nanopore, that is, a method for producing a nanopore before solution introduction and a method for producing a nanopore after solution introduction. In the case of producing the nanopore before solution introduction, a method in which an electron beam such as TEM or etching is used to open a pore as in NPTL 1. In the case of producing a nanopore after solution introduction, a method in which a high voltage is applied to a thin film to perform dielectric breakdown of the thin film and open a pore as in NPTL 2. After the nanopore is produced by any of the above methods, a subject is introduced into a solution, and a signal when the subject passes through the nanopore is acquired.

CITATION LIST

Non-Patent Literature

NPTL 1: Venta, K., et al., Differentiation of Short, Single-Stranded DNA Homopolymers in Solid-State nanopores, ACS Nano 7 (5), pp. 4629-4636 (2013).

NPTL 2: Yanagi, I., et al., Fabricating nanopores with diameters of sub-1 nm to 3 nm using multilevel pulse-voltage injection, Sci. Rep., 4 (5000) (2014).

SUMMARY OF INVENTION

Technical Problem

FIGS. 1 and 2 illustrate typical measurement procedures of a solid-state nanopore sequencer. In the procedure illustrated in FIG. 1, a surface is hydrophilized after a nanopore is produced using an electron beam such as TEM or etching, a solution is introduced, and then a subject is introduced into the solution and measured. In the procedure illustrated in FIG. 2, a surface is hydrophilized, a solution is introduced, then a nanopore is produced using dielectric breakdown, and a subject is introduced into the solution and measured. If time such as one day or more elapses between the hydrophilic treatment and the solution introduction, the hydrophilicity of a device surface is gradually attenuated due to adhesion of organic matter or the like in the atmosphere to the surface so that it becomes difficult for a film surface to be filled with a liquid. Therefore, it is necessary to introduce the solution within one day after the hydrophilic treatment.

Assuming a case where the nanopore sequencer is sold as a product from a manufacturer to a customer, and whether a process described in FIGS. 1 and 2 corresponds to a manufacturer-side process or a customer-side process is considered. In general, $O_2$ plasma or the like is used in the hydrophilic treatment process, and it is difficult for a customer to perform the treatment, and thus, it is desirable that the treatment is performed on the manufacturer side in order to lower a device unit price. On the other hand, a biological molecule introduction process needs to be performed on the customer side such that the customer can input a sample to be measured. Therefore, it is necessary to transport a device from the manufacturer to the customer between the hydrophilic treatment and the biological molecule introduction process. Considering the time for transport to overseas or the like, it is assumed that this transport process takes about a week. Considering the time for storage of the device for two to three weeks at the customer side, it is assumed that it takes a week to a month or more from the hydrophilic treatment process to a biological molecule introduction process. In the present specification, the term "storage" means a process until a potential difference is applied to a thin film by an external power source or the like, and biomolecular property analysis is performed. It is generally difficult to maintain hydrophilicity of a device surface for a week to a month or more.

Therefore, a procedure of introducing a solution on the manufacturer side after hydrophilic treatment and then performing transport to the customer can be considered as illustrated in FIGS. 3 and 4. Such a method can protect the adhesion of organic matter in the atmosphere with the solution, and thus, transport to the customer can be performed while maintaining the hydrophilicity, and long-term storage on the customer side is also possible. Further, this procedure eliminates the need for introducing the solution on the customer side and eliminates the need for a solution introduction mechanism on the customer side, thereby reducing cost of the device.

However, it has been found that when a thin film containing Si is immersed in an aqueous solution, a dielectric breakdown voltage decreases over time so that a film quality deteriorates. If the dielectric strength of the film decreases, problems occur. Dielectric breakdown of the film occurred due to a potential difference applied to the film caused by the influence of static electricity. In addition, energy required to produce a nanopore by applying high energy to the thin film changes (for example, a change of a dielectric breakdown voltage that needs to be applied when producing a nanopore by dielectric breakdown or a change of power of an electron beam when producing a nanopore by TEM) so that it is difficult to control a nanopore diameter. Further, the nanopore diameter increases over time due to an applied voltage (0.1 to 0.5 V or the like) to the nanopore during biological sample measurement. Such a deterioration phenomenon has not been reported so far so that a cause of the deterioration has not been clarified, and a method for preventing the deterioration is also unknown.

Solution to Problem

As an aspect, an apparatus for storing a thin film device of the present invention includes: a thin film device having an insulating thin film containing Si and having a thickness of 100 nm or less; a solution in contact with the thin film; and a container having a tank that seals the solution, wherein the solution is a solution that satisfies any of the following conditions (1) to (3).

(1) A solution containing water in a volume ratio of 0% or more to 30% or less (2) A solution cooled and maintained at a temperature equal to or higher than a solidification point and lower than 15° C.

(3) A solution that contains a salt with a concentration of 1 mol/L or more and a saturation concentration or less and is cooled and maintained to a temperature equal to or higher than a solidification point and lower than 25° C.

As one aspect, a method for storing a thin film device of the present invention is a method for storing a thin film device having an insulating thin film containing Si and having a thickness of 100 nm or less, and includes: a step of hydrophilizing the thin film device; and a step of storing the hydrophilized thin film device in contact with a solution that satisfies any of the above conditions (1) to (3).

Further, as an aspect, a method for measuring a biological molecule of the present invention includes: a step of storing a thin film device having an insulating thin film, which contains Si, does not have a pore, and has a thickness of 100 nm or less in contact with a solution that satisfies any of the above conditions (1) to (3); a step of forming a pore in the thin film by applying a voltage equal to or higher than a dielectric breakdown voltage of the thin film between a first electrode and a second electrode, the first electrode coming into contact with the solution in contact with one surface of the thin film device and the second electrode coming into contact with the solution in contact with the other surface; a step of introducing a biological molecule into the solution in contact with the first electrode or the solution in contact with the second electrode; and a step of giving a potential difference between the first electrode and the second electrode and measuring a change of a current value during passage of the biological molecule through the pore to examine a characteristic of the biological molecule.

Advantageous Effects of Invention

According to the present invention, it is possible to prevent a decrease of a dielectric breakdown voltage that occurs when an insulating thin film containing Si is immersed in a solution.

Other objects, configurations, and effects which have not been described above become apparent from embodiments to be described hereinafter.

DESCRIPTION OF EMBODIMENTS

Figure 1:
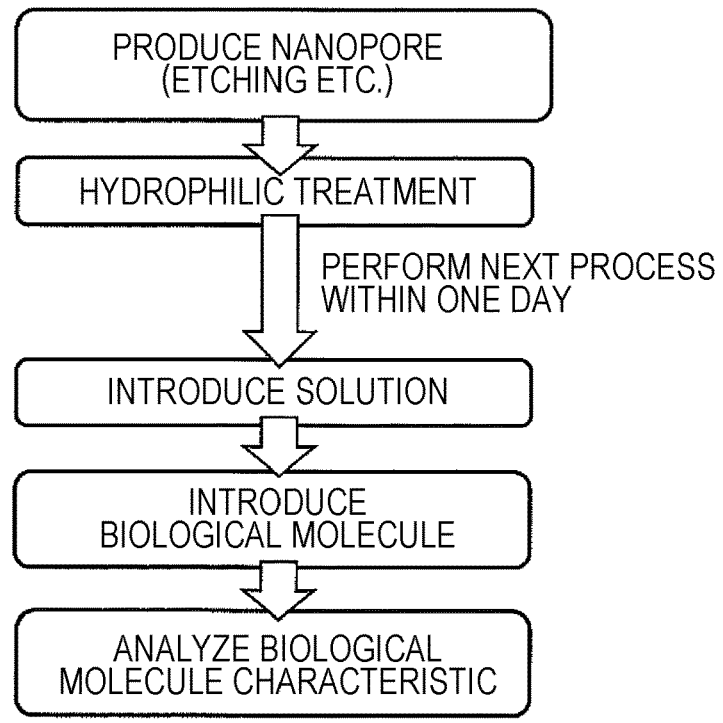
FIG. 1 is a view illustrating a biological molecule measurement procedure using a general nanopore.
Figure 2:
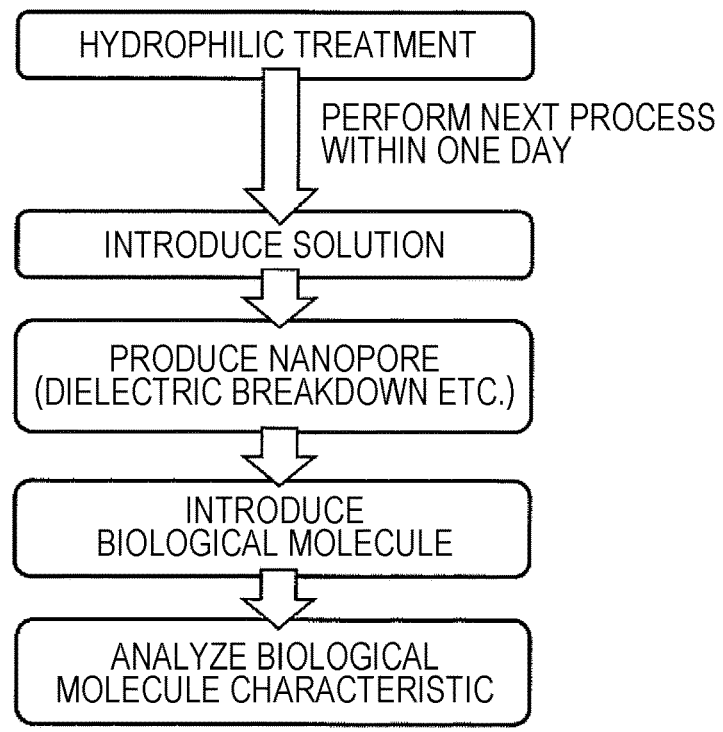
FIG. 2 is a view illustrating a biological molecule measurement procedure using a general nanopore.
Figure 3:
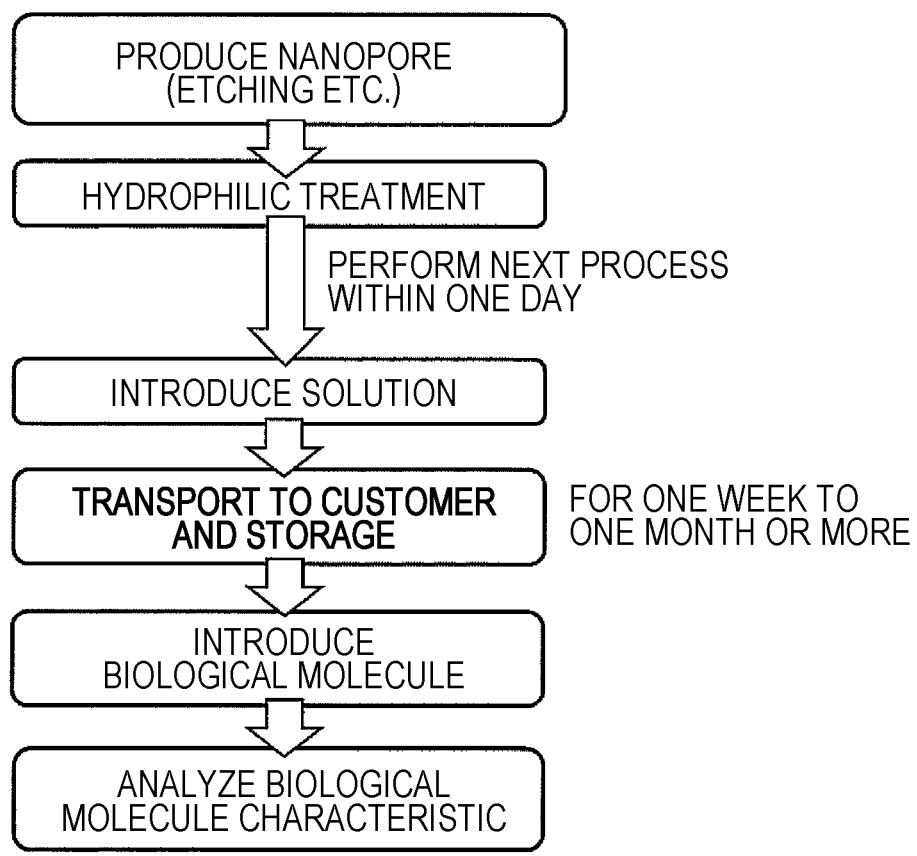
FIG. 3 is a view illustrating a biological molecule measurement procedure using a nanopore accompanied by transportation to a customer and storage.
Figure 4:
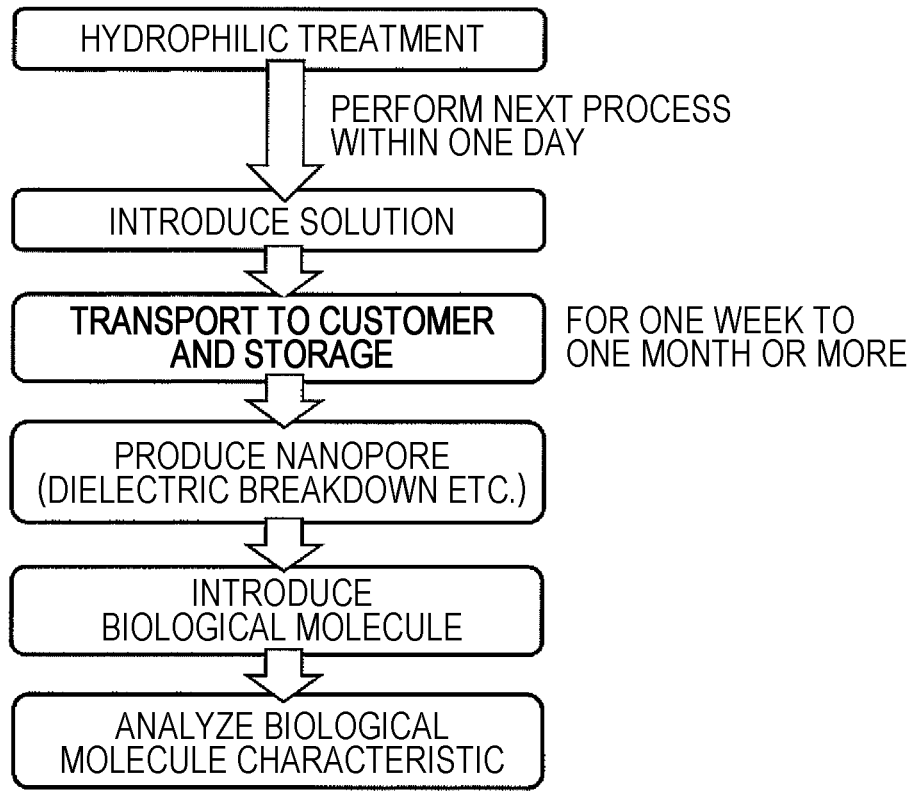
FIG. 4 is a view illustrating a biological molecule measurement procedure using a nanopore accompanied by transportation to a customer and storage.

Hereinafter, embodiments of the present invention will be described with reference to the drawings. Incidentally, the same reference numerals will be attached to those having the same function in the entire drawing for describing the embodiments, and the repetitive description thereof will be omitted if possible. Further, the present invention is not construed as being limited to the description of the embodiments to be described below. Those skilled in the art can easily understand that specific configurations can be changed without departing from the spirit or gist of the present invention.

Positions, sizes, shapes, ranges, and the like of the respective components illustrated in the drawings and the like do not always indicate actual positions, sizes, shapes, ranges and the like in order to facilitate understanding of the invention. Therefore, the present invention is not necessarily limited to the positions, sizes, shapes, ranges, and the like disclosed in the drawings and the like.

The publications and patent applications cited in the present specification constitute a part of the description of the present specification as they are.

Components expressed by the singular in the present specification are intended to include the plural unless clearly indicated in the context.

Figure 5:
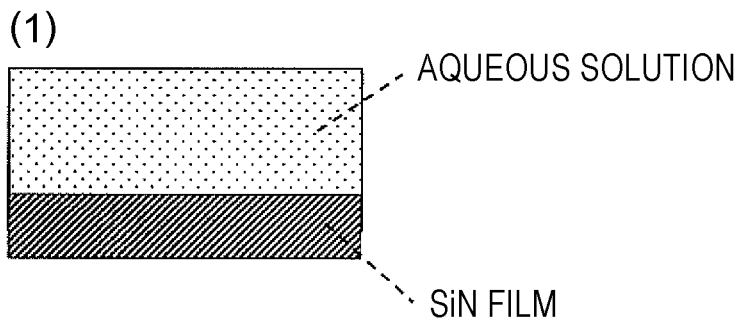
FIGS. 5(1) and 5(2) are explanatory views illustrating a mechanism for decreasing a dielectric breakdown voltage of a SiN film.
Figure 5:
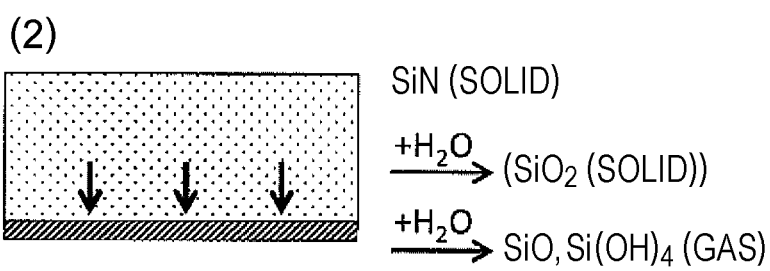

Here, a mechanism by which a dielectric breakdown voltage of an insulating thin film containing Si is decreased was first estimated and verified, and a solving method based on the mechanism was studied. It is known that a Si film is oxidized by water vapor in the air, and further, an oxide film reacts with the water vapor and eventually volatilizes when the film containing Si (such as a SiN film) is placed in an environment such as a high temperature, a high pressure, and a high humidity. Although a storage environment of the Si film used in the present embodiment does not correspond to the high temperature and high pressure, a large amount of $H_2O$ exists in the vicinity of the film, and it is considered that an etching reaction as illustrated in FIG. 5 proceeds by contact with solution for a long time. When the film containing Si is etched by $H_2O$, the film becomes thinner so that the dielectric breakdown voltage decreases. Further, it is considered that the problem of the decrease of the dielectric breakdown voltage has become obvious due to slight etching since a thickness of the Si film used in a solid-state nanopore sequencer or the like is thin.

Subsequently, a life of a thin film device (hereinafter simply referred to as a device life) according to the etching reaction illustrated in FIG. 5 was formulated, and a method of extending the life was considered. The thin film used in a measurement device using a solid-state nanopore generally has a thickness of 100 nm or less, and a thin film having a thickness of 10 nm or less is used when measuring a sample such as DNA. In such measurement, the device life is defined as a time [h/V] until a dielectric breakdown voltage decreases by 1 V since a decrease of the breakdown voltage by 1 V or more generally means that a thickness has become thinner than 1 nm, which causes a great change of a film characteristic. The etching reaction illustrated in FIG. 5 (n-order reaction of $H_2O$: $SiN+nH_2O \rightarrow SiO$, $Si(OH)_4$, $n \geq 1$) follows the Arrhenius equation, and thus, the device life Lt [h/V] can be expressed as the following formula.

$$Lt = A \times e^{E/RT} \times [H_2O]^{-n} \quad \text{(Formula 1)}$$

Here, $[H_2O]$ is an $H_2O$ concentration [mol/L], T is an absolute temperature [K], E is activation energy [J/mol], and A and R ($\approx$#8.314 J/(mol·K)) are constants.

From the above formula, it has been found that any countermeasure of (i) a decrease of $[H_2O]$, (ii) a decrease of T, and (iii) an increase of E is required to increase Lt. As specific countermeasures, the increase of Lt can be realized by setting conditions for a solution in contact with the thin film device as: (i) an organic solvent (solution with a low $H_2O$ concentration), (ii) a low-temperature solution, and (iii) a solution containing a high-concentration salt. Regarding (iii), an aqueous solution containing a salt is stabilized in a state where the salt is hydrated, and it is necessary to perform dehydration from the salt in order for water to etch the thin film. Therefore, E can be increased by the hydration energy of the salt. The verification of the above hypothesis will be described based on experimental results to be described later. Further, details of the device life obtained under the conditions (i), (ii), and (iii) will also be described based on the experimental results to be described later.

As described above, as the thin film device is stored using the solution satisfying any condition of (i) the solution with a low $H_2O$ concentration, (ii) the low-temperature solution, and (iii) the solution containing a high-concentration salt as the solution in contact with the thin film containing Si, it is possible to prevent deterioration of the thin film while maintaining hydrophilicity of a surface of the thin film device. (i) The solution having a low $H_2O$ concentration is typically an organic solvent, and a solution containing ethanol, methanol, 2-propanol, DMSO, or the like can be typically used. Examples being sold include 99.5% ethanol, 99.8% methanol, 99.7% 2-propanol, 99.5% DMSO, and the like, and such solutions may be used. Further, (i) the solution having a low $H_2O$ concentration or (ii) the low-temperature solution may be a solution containing about 1 mol/L or less of a salt such as LiCl, NaCl, KCl, RbCl, $MgCl_2$, $CaCl_2$, $SrCl_2$, and $BaCl_2$. The solutions (i), (ii), and (iii) may contain a plurality of types of reagents, and may contain, for example, a pH adjuster or an enzyme.

Since it takes about a week for delivery to a customer as described above, a device life needs to be a week or more. In order to achieve the device life of a week or more, it is desirable that the solution in contact with the Si-containing thin film satisfy any solution condition of (1) a solution containing water in a volume ratio of 0% or more to 30% or less, (2) a solution having a temperature equal to or higher than a solidification point and lower than 15° C., and (3) a solution that contains a salt with a concentration of 1 mol/L or more and a saturation concentration or less and has a temperature equal to or higher than a solidification point and lower than 25° C. A basis for such numerical values will be described later.

Further, it is preferable that the thin film device can be not only transported but also be stored and measured on the customer side, and it is preferable to enable the storage for two to three weeks or more as a practical operation method. Thus, it is preferable to enable the storage for a month or more in total when considering a week required for delivery. In order to achieve the device life of a month or more, it is preferable to satisfy any condition of (4) a solution containing water in a volume ratio of 0% or more to 5% or less, (5) a solution having a temperature equal to or higher than a solidification point and lower than 5° C., and (6) a solution that contains a salt with a concentration of 1 mol/L or more and a saturation concentration or less and has a temperature equal to or higher than a solidification point and lower than 15° C. A basis for such numerical values will be described later, which is similar to (1), (2), and (3) above.

Incidentally, storage conditions for the solution with a low $H_2O$ concentration were calculated as follows. When a device life with the solution with a low $H_2O$ concentration is Lt', and the $H_2O$ concentration is [$H_2O$'], a volume ratio of water ([$H_2O$']/[$H_2O$]) can be expressed by the following formula.

$$[H_2O']/[H_2O]=(Lt/Lt')^{1/n} \geq Lt/Lt' \qquad \text{(Formula 2)}$$

With this formula, a minimum volume ratio of water ([$H_2O$']/[$H_2O$]) required to obtain a target Lt' can be calculated if the device life Lt at a certain temperature is measured. Here, the device life Lt during storage in pure water at 25° C. was calculated from results illustrated in FIG. 21 to be described later, and the volume ratio required to obtain Lt'≥1 week or Lt'≥1 month was calculated. As a result, the above conditions (1) and (4) were obtained.

Figure 6:
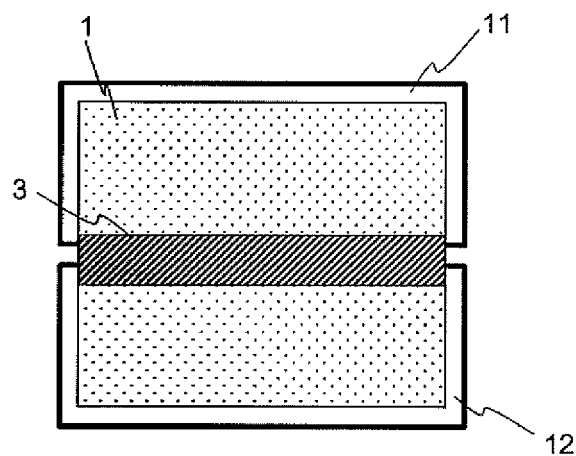
FIG. 6 is a schematic cross-sectional view illustrating a configuration example of an apparatus for storing a thin film device.

FIG. 6 is a schematic cross-sectional view illustrating a configuration example of the apparatus for storing the thin film device according to the present embodiment. Further, FIGS. 7 to 15 are schematic cross-sectional views illustrating other configuration examples of the apparatus for storing the thin film device.

As illustrated in FIG. 6, the apparatus for storing the thin film device has a container including a first tank 11 and a second tank 12 and holds a thin film device that needs to be stored. A solution 1 is sealed in the first tank 11 and the second tank 12 of the container. In the case of FIG. 6, the thin film device is drawn as a thin film 3. The thin film 3 is in contact with the solution 1 with one surface disposed in the first tank 11 of the container and the other surface disposed in the second tank 12, and the solution 1 filled in the first tank 11 and the second tank 12 is separated by the thin film 3. The solution 1 satisfies any of the above conditions (1) to (3) that can achieve the device life of a week or more, and preferably is a solution that satisfies any of the above conditions (4) to (6) that can achieve the device life of a month or more. Two or more of the conditions (1) to (6) may be satisfied at the same time such that the life can be made longer.

Further, it is preferable that the solution 1 can be used as a solution at the time of applying a voltage by connecting an electrode to the solution 1 in a process after storage, and the solution 1 is preferably a solution containing a salt of 1 mmol/L or more to be used in general nanopore measurement. When the solution 1 is the solution containing a salt less than 1 mmol/L, electric conductivity is low, a sufficient current cannot be obtained even if a voltage is applied so that it is difficult to measure the current. Thus, a process of replacing the solution 1 with the solution containing a salt of 1 mmol/L or more is required before applying a voltage. Further, it is desirable to increase the salt concentration such that the electrical conductivity increases in order to improve a signal during the current measurement. The salt concentration is preferably 10 mmol/L or more, and more preferably 100 mmol/L or more. As a cation contained in the solution 1, ionizing cations can be used, and typically, it is preferable to use a Group I element or a Group II element such as Li, Na, K, Rb, Cs, Mg, Ca, Sr, and Ba. As an anion contained in the solution 1, ionizing anions can be used, and it is preferable to select the anion based on the compatibility with an electrode material. For example, when silver halide is used as the electrode material, it is preferable to use halide ions such as I, Br and Cl as the anion. Further, the anion may be organic anions represented by glutamate ion or the like.

Figure 7:
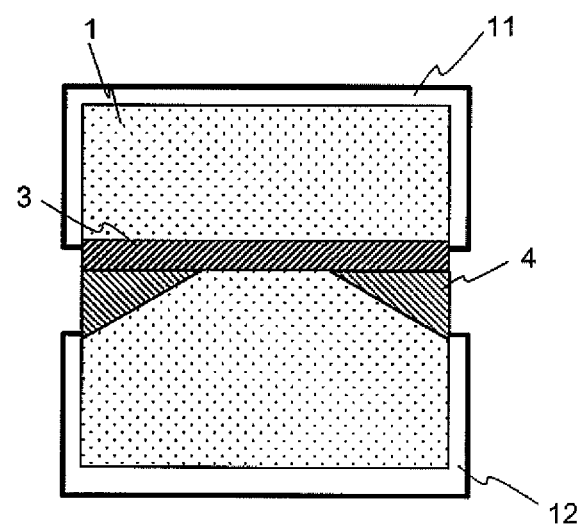
FIG. 7 is a schematic cross-sectional view illustrating a configuration example of an apparatus for storing a thin film device.

The thin film 3 is made of an inorganic material, and the inorganic material is desirably any material that can be formed by a semiconductor micromachining technique. The inorganic material is typically silicon nitride, silicon oxide, hafnium oxide, molybdenum disulfide, graphene, or the like, and is preferably silicon nitride, silicon oxide, and the like which are Si compounds that can be mass-produced by a semiconductor process. In general, the thin film 3 is likely to be mechanically broken by vibrations and shocks generated in a process of being gripped with tweezers, and thus, a support structure 4 that supports the thin film 3 is preferably provided as illustrated in FIG. 7. As the structure to support the thin film 3, for example, a silicon support substrate having a thickness of about 725 μm can be used. For example, a thin film device in which a SiN thin film having a thickness of 1 μm or less and an area of 100 μm$^2$ or less is supported by a support substrate is used. The thin film device referred to in the present specification may be configured only using the thin film made of the inorganic material in this manner, but preferably includes the thin film and the support structure to support the thin film.

When the thin film 3 is etched with an aqueous solution, it is considered as a significant change if a thickness changes by 1% or more from the original thickness. Thus, a change of a dielectric breakdown voltage of 1 V or more (that is, a thickness of 1 nm or more) becomes a problem when a thin film having a thickness of 100 nm or less is used. That is, the storage in the solution 1 in the present embodiment is particularly effective for the thin film having a thickness of 100 nm or less, and is more effective for an ultra-thin film having a thickness of 10 nm or less that may change by 10% or more from the original thickness.

It is preferable to determine a thickness of the thin film 3 more strictly according to a measurement content, and it is necessary to set the thickness to 0.1 nm or more to 100 nm or less. When a biopolymer or the like is analyzed as a subject, the thickness is set to a thickness of two times or more, preferably three times or more, and more preferably five times or more of a monomer unit constituting the biopolymer. For example, when the biopolymer is made of a nucleic acid, the thickness is preferably set to a size of three or more bases, for example, about 1 nm or more. Meanwhile, from the viewpoint of the resolution of a nanopore sensor, it is preferable that a thickness of a nanopore be thin in order to grasp a shape and a constituent material of the biopolymer (a base species or the like in the case of DNA). For example, it is preferable to set the thickness of the nanopore to be 100 nm or less in order to measure a *streptococcus* or the like having a biopolymer size of about 1 to 10 μm and grasp a linearly continuous shape thereof. Furthermore, the thickness of the nanopore is set preferably to 30 nm or less, and more preferably to 10 nm or less in order to analyze a base species of DNA when a biopolymer is made of a nucleic acid since an interval between bases is as short as 0.5 nm. As a result, it is possible to analyze the shape, the constituent material, or the like of the biopolymer with high resolution. Further, a shape of the nanopore is basically circular, but can be also elliptical or polygonal.

The solution 1 needs to be filled after processing to allow a liquid to come into contact with a surface of the thin film 3. Specifically, it is desirable to use a method of filling the solution 1 after applying $O_2$ plasma to the surface of the thin film 3 to make the surface hydrophilic, a method of filling the solution 1 after removing organic residues with a piranha solution or the like to make the surface hydrophilic, a method of filling the solution 1 by filling the surface of the thin film once with a solution having a small surface tension, such as ethanol, and then replacing the solution with the solution 1, or the like.

A plurality of thin film portions that analyzes a biopolymer may be arrayed to be arranged side by side. A nanopore array structure has an advantage that a measurement throughput can be dramatically increased. In this nanopore array structure, it is preferable to regularly arrange the thin film portions having nanopores. An interval to dispose the plurality of thin film portions can be set to 0.1 μm to 10 μm, and preferably 0.5 μm to 4 μm according to an electrode to be used, the capacity of an electrical measurement system, a processing limit of the semiconductor process, or the like.

A material of a solution tank, such as the first tank 11 and the second tank 12, may be, for example, PMMA or may be made of Teflon (registered trademark) having excellent chemical resistance. Each solution tank having the capacity of, for example, 100 mL or less is used.

Figure 8:
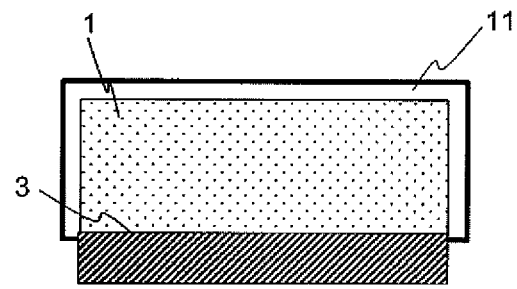
FIG. 8 is a schematic cross-sectional view illustrating a configuration example of an apparatus for storing a thin film device.
Figure 9:
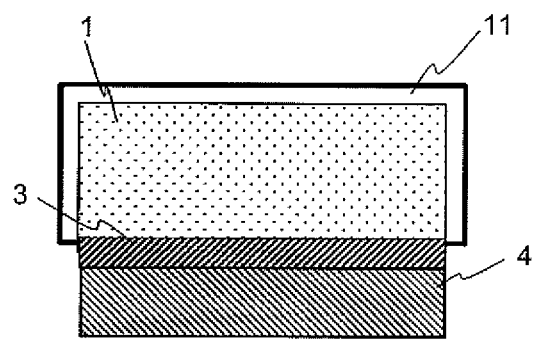
FIG. 9 is a schematic cross-sectional view illustrating a configuration example of an apparatus for storing a thin film device.

FIGS. 6 and 7 describe a configuration in which a solution is filled on both sides of the thin film 3 as used in a sensor such as a nanopore DNA sequencer. However, as a matter of course, a phenomenon that the solution etches the thin film 3 occurs even when the solution is filled only on one side of the thin film 3 as illustrated in FIG. 5. Therefore, an effect of preventing etching described in the present specification can be obtained even when the solution 1 is filled only on one side of the thin film 3 as illustrated in FIG. 8. An apparatus for storing a thin film device illustrated in FIG. 8 has a container including the first tank 11 and holds a thin film device that needs to be stored. The solution 1 is sealed in the first tank 11 of the container. In the case of FIG. 8, the thin film device is drawn as the thin film 3. The configuration of FIG. 8 is used in a sensor such as an ion sensitive field effect transistor sensor (ISFET). The ISFET is a FET in which a gate surface is covered with an ion sensitive film, and detects a surface potential between the solution and the ion sensitive film. The insulating thin film 3, such as $SiO_2$, SiN, and $Al_2O_3$, is used for the ion sensitive film of the ISFET. Note that there is a condition that a thickness of the insulator is about 1 to 100 nm. Therefore, it is preferable to provide the support structure 4 to support the thin film 3 as illustrated in FIG. 9. As the structure to support the thin film 3, for example, a silicon support substrate having a thickness of about 725 μm or the like can be used. In order to cause the sensor illustrated in FIG. 9 to function as the FET, it may be configured such that a source electrode and a drain electrode are provided on a Si support substrate, and an insulating film such as, $SiO_2$ and SiN, is provided on the source electrode and the drain electrode. The thin film device referred to in the present specification may be configured only using the thin film made of the inorganic material in this manner, but preferably includes the thin film and the support structure to support the thin film.

Even in the configuration in which the solution is filled on one side of the thin film 3 as illustrated in FIGS. 8 and 9, the thin film 3 is gradually etched from a site in contact with the solution, and sensor characteristics change. Thus, it is necessary to consider conditions of the solution 1 in the same manner as in the configurations of FIG. 6 or 7 in order to extend a device life. Regarding the device life that needs to be achieved in the configuration in which the solution is filled on one side of the thin film 3, the device life needs to be a week or more since it takes about a week for delivery to the customer. Further, it is preferable that the thin film device can be not only transported but also be stored and measured on the customer side, and it is preferable to enable the storage for two to three weeks or more as a practical operation method. Thus, it is preferable to enable the storage for a month or more in total when considering a week required for delivery. When comparing a device life when the solution is filled on one side of the thin film 3 with a device life when the solution is filled on both sides of the thin film 3, the device life is longer when the solution is filled on one side since the etching proceeds from the site where the thin film 3 in contact with the solution. Accordingly, it is sufficient to satisfy any of the above conditions (1) to (3), which are the solution conditions when achieving the device life of a week or more at the time of filling the solution on both sides in order to set the device life to a week or more. Further, it is desirable to satisfy any of the above conditions (4) to (6) in order to achieve a device life of a month or more.

Figure 10:
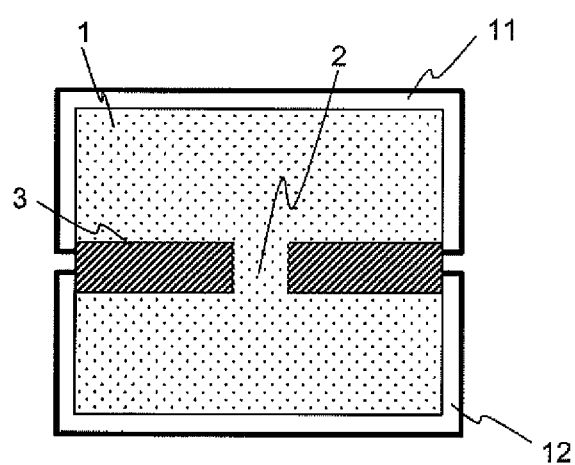
FIG. 10 is a schematic cross-sectional view illustrating a configuration example of an apparatus for storing a thin film device.

Configurations illustrated in the drawings in FIG. 10 and the subsequent drawings are obtained by assuming an application to a sensor such as a nanopore DNA sequencer, and a configuration in which a solution is filled on both sides of a thin film is described. As illustrated in FIG. 10, a nanopore 2 may be provided in the thin film 3, and the nanopore 2 may be formed by a semiconductor process so as to enable mass production or may be formed with a TEM electron beam such that the pore diameter is small. More preferably, it is desirable to use the nanopore 2 formed by dielectric breakdown by applying a high voltage to the thin film 3 such that the nanopore with a small pore diameter can be formed accurately, quickly, and inexpensively. When the nanopore is provided in the thin film at the stage of incorporation into the container in this manner, there is no need to produce the nanopore on the customer side when this storage apparatus is delivered to a customer, the apparatus configuration is simplified, and measurement is possible immediately.

It is preferable to determine a diameter of the nanopore more strictly according to a measurement content. For example, the diameter is 100 nm or less in the case of analyzing a biopolymer or a bead having a diameter of about 10 nm, preferably 50 nm or less, and specifically about 0.9 nm to 10 nm. For example, a diameter of a nanopore to be used for analysis of single-stranded DNA having a diameter of about 1.4 nm is preferably about 1.4 nm to 10 nm, and more preferably about 1.4 nm to 2.5 nm. Further, for example, a diameter of a nanopore to be used for analysis of double-stranded DNA having a diameter of about 2.6 nm is preferably about 3 nm to 10 nm, and more preferably about 3 nm to 5 nm.

Figure 11:
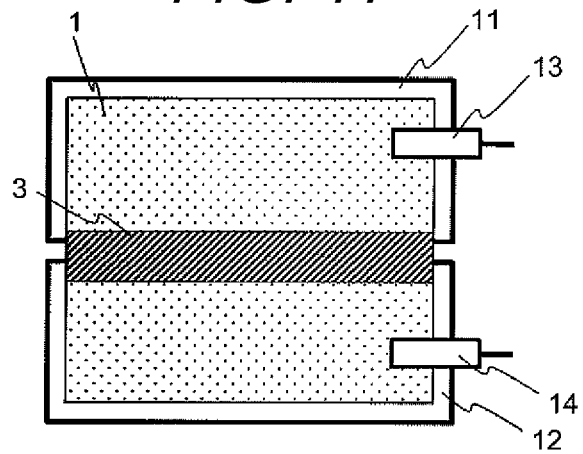
FIG. 11 is a schematic cross-sectional view illustrating a configuration example of an apparatus for storing a thin film device.
Figure 12:
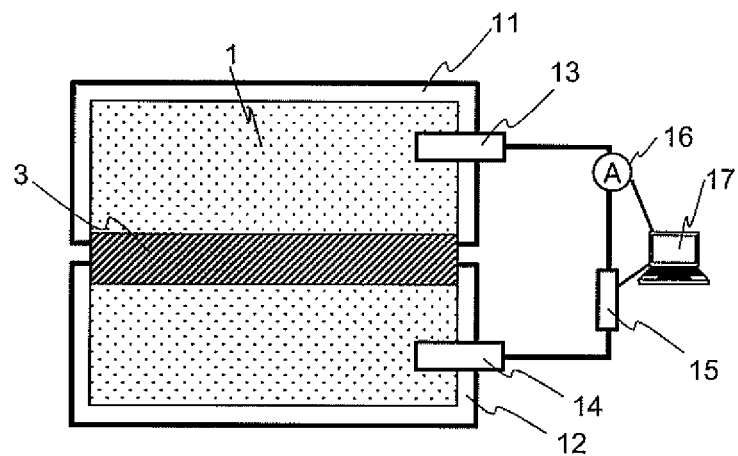
FIG. 12 is a schematic cross-sectional view illustrating a configuration example of an apparatus for storing a thin film device.

As illustrated in FIG. 11, in a state where a first electrode 13 and a second electrode 14 are provided in the first tank 11 and the second tank 12, respectively, the first electrode 13 is in contact with a solution in the first tank 11 and the second electrode 14 is in contact with a solution in the second tank 12, this makes easy to be connected to a circuit system including a power supply device 15, an ammeter 16, and a control and measurement device 17 separately provided outside the liquid tanks as illustrated in FIG. 12. The control and measurement device 17 may be a PC. When the apparatus for storing the thin film device with the structure illustrated in FIG. 11 is adopted, measurement can be performed at low cost, for example, if only one apparatus constituted by the power supply device 15, the ammeter 16 and the control and measurement device 17 is prepared, the apparatus for storing the thin film device is utilized as a consumable, and a new apparatus for storing a thin film device is used every time measurement is completed. That is, the apparatus for storing the thin film device provided with the electrodes 13 and 14 is used not only for storage of the thin film device but also for use in current measurement.

The electrode, such as the first electrode 13 and the second electrode 14, is preferably made of a material capable of performing an electron giving/receiving reaction (Faraday reaction) with an electrolyte in the solution 1, and is typically made of silver halide or alkali silver halide. Silver chloride is preferably used for the electrode from the viewpoint of potential stability and reliability. The electrode may be made of a material that becomes a polarization electrode, for example, gold, platinum, or the like. In such a case, it is preferable to add a material that can assist the electron giving/receiving reaction in the solution, for example, potassium ferricyanide, potassium ferrocyanide, or the like in order to ensure a stable ionic current. Alternatively, it is preferable to immobilize a material capable of performing the electron giving/receiving reaction, for example, ferrocenes, on a surface of a polarization electrode.

As for a structure of the electrode, the entire electrode may be made of the above-described materials, or a surface of a base material, such as copper and aluminum, may be coated with the above-described materials. A shape of the electrode is not particularly limited, but a shape that increases the surface area in contact with the solution is preferable. The electrode is joined to a wiring, and an electrical signal is sent to a measurement circuit. The power supply device 15 may be connected to the control and measurement device 17 such that an application voltage can be controlled, and a measurement system that stores a measured current as data may be configured by also connecting the ammeter 16 to a device such as a personal computer. The ammeter 16 may include an amplifier that amplifies a current flowing between the electrodes by applying a voltage and an analog to digital converter (ADC).

Figure 13:
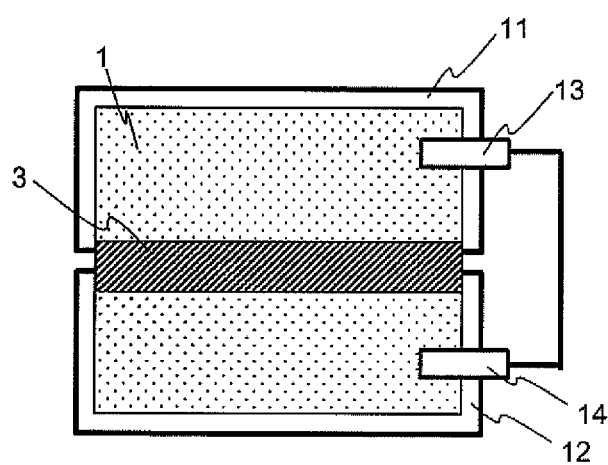
FIG. 13 is a schematic cross-sectional view illustrating a configuration example of an apparatus for storing a thin film device.

If a large potential difference between the first electrode 13 and the second electrode 14 leads to a dielectric breakdown failure of the thin film 3, and thus, it is necessary to adjust at least the potential difference to be kept at dielectric strength of the thin film or less. The dielectric strength of the thin film is generally 1 V/nm and needs to be kept at this electric field strength or less. It is preferable to adjust the potential difference between the first electrode 13 and the second electrode 14 to be less than a dielectric breakdown voltage of the thin film, such as 0 V, so that no voltage is applied to the film over time. It is desirable to adopt a structure in which the first electrode 13 and the second electrode 14 are short-circuited as illustrated in FIG. 13.

Figure 14:
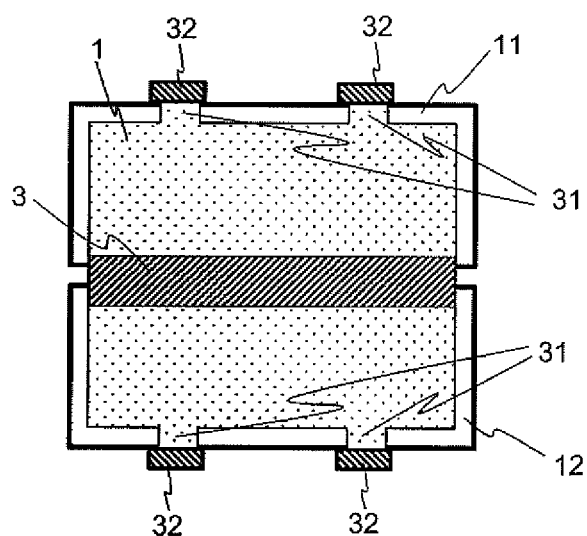
FIG. 14 is a schematic cross-sectional view illustrating a configuration example of an apparatus for storing a thin film device.

Further, the container is preferably provided with introduction and discharge ports 31 as illustrated in FIG. 14 in order to easily introduce the solution 1 into the first tank 11 and the second tank 12. There is a possibility that the solution 1 volatilizes over time through the introduction and discharge ports 31, and thus, it is desirable that the container have a sealing structure for volatilization prevention. Specifically, the structure is adopted such that a sealing structure 32 is provided at a flow path introduction port of the container, that is, a solution 32 (an organic solvent such as benzene/fluorinate if the solution 1 is an aqueous solution) that is not mixed with the solution 1 is disposed. The structure is constructed by a procedure of, for example, filling the solution 1 previously up to the vicinity of the introduction and discharge ports 31, and then, dropping the solution 32 so as to cover the introduction and the discharge ports 31 when disposing the solution 32. It is preferable that the area where the solution 1 comes into contact with air be reduced.

Figure 15:
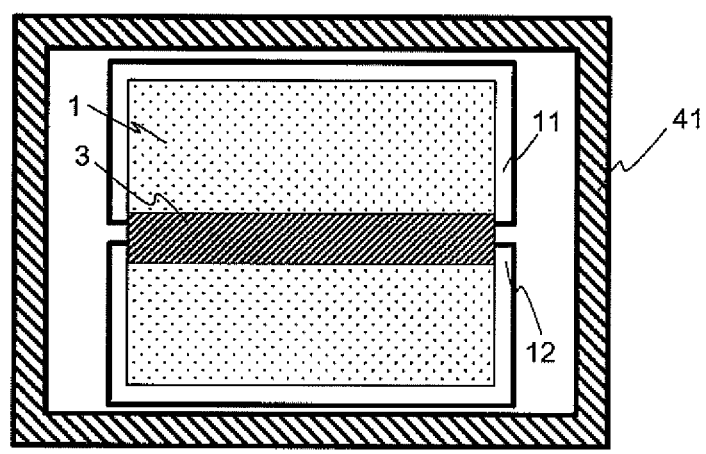
FIG. 15 is a schematic cross-sectional view illustrating a configuration example of an apparatus for storing a thin film device.

It is necessary to provide a temperature adjustment mechanism in order to cool the solution 1 to a low-temperature solution. Specifically, any temperature adjustment mechanism in which a heat transfer element (such as a Peltier element) is attached to the container of the apparatus for storing the thin film device to transfer heat to the solution 1 through the heat transfer element and the container is desirably adopted. However, unit cost is likely to increase in the form of attaching the Peltier element or the like to the container of the apparatus for storing the thin film device since it is necessary to prepare the Peltier element for each container. Therefore, it is preferable to adopt a form in which a temperature adjustment mechanism 41 is disposed around the container holding the thin film device as illustrated in FIG. 15. Specifically, a thermostatic bath, a cold insulation material, dry ice, or the like is provided or the apparatus for storing the thin film device is placed in a refrigerator or a freezer. As an aspect of delivering the above-described apparatus for storing a thin film device from the manufacturer side to the customer side and storing the apparatus on the customer side, for example, the delivery is performed in a state where the cold insulation material or dry ice is disposed around the apparatus for storing the thin film device, and the apparatus is stored in the refrigerator or freezer on the customer side.

Figure 16:
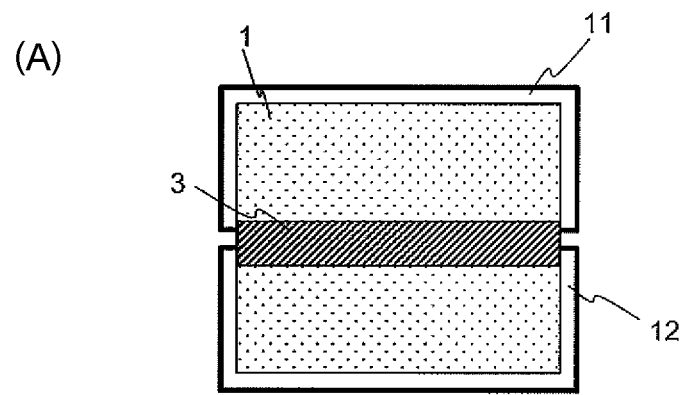
FIGS. 16(A)-16(C) are schematic views illustrating a method for measuring a biological molecule using a stored thin film device.
Figure 16:
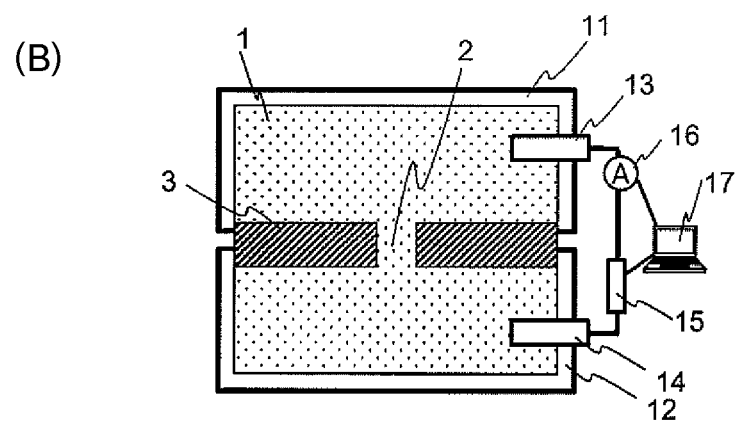
Figure 16:
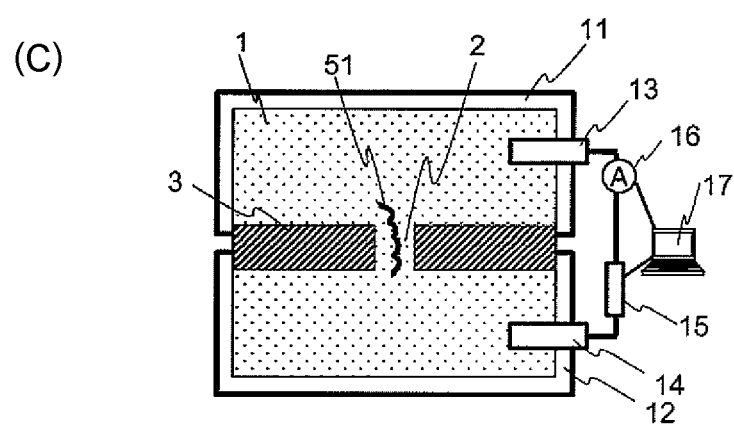

FIG. 16 is a schematic view illustrating a method for measuring a biological molecule using a thin film device stored in the apparatus for storing the thin film device according to the present embodiment. First, the thin film is brought into contact with the solution 1 as illustrated in FIG. 16(A). At this time, the thin film 3 is prevented from deteriorating by using the solution 1, and thus, processing such as transport of this storage apparatus from the manufacturer to the customer over a long period of time or storing the apparatus for a long time may be performed.

Subsequently, as illustrated in FIG. 16(B), a high voltage equal to or higher than a dielectric breakdown voltage of the thin film 3 is applied between the first electrode 13 and the second electrode 14 by an apparatus constituted by the power supply device 15, the ammeter 16, and the control and measurement device 17, or the like, thereby forming the nanopore 2 in the thin film 3 by dielectric breakdown. Finally, as illustrated in FIG. 16(C), a biopolymer 51, such as DNA, is introduced into the solution in contact with the first electrode 13 or the solution in contact with the second electrode 14 to give a potential difference between the first electrode 13 and the second electrode 14, and a biological sample is measured and analyzed based on a change of an ionic current during passage of the biopolymer 51 through the nanopore 2.

In the apparatus for storing the thin film device illustrated in FIG. 16(A), the first electrode 13 and the second electrode 14 are provided in the first tank 11 and the second tank 12, respectively, as illustrated in FIG. 11. The first electrode 13 may be in contact with the solution in the first tank 11, and the second electrode 14 may be in contact with the solution in the second tank 12. With such a configuration, it is possible to easily connect the apparatus to the circuit system constituted by the power supply device 15, the ammeter 16, and the control and measurement device 17 separately provided outside the liquid tank. Alternatively, the thin film device stored in the apparatus for storing the thin film device illustrated in FIG. 16(A) provided with no electrode may be taken out of the apparatus for storing the thin film device during measurement and installed in a container for measurement provided with the electrode illustrated in FIG. 16(B).

The biopolymer 51 to be analyzed is desirably an object that changes an electrical characteristic, particularly a resistance value during passage through the nanopore 2, and is made of a nucleic acid. Specifically, examples of the biopolymer 51 include RNA (single-stranded RNA or double-stranded RNA), DNA (single-stranded DNA or double-stranded DNA), PNA (peptide nucleic acid), an oligonucleotide, an aptamer, and a combination thereof (for example, a hybrid nucleic acid). The biopolymer 51 may be one that is present in a living body or one that is derived from those present in the living body. For example, examples of the biopolymer 51 also include a sequence that does not exits naturally or a polymer containing a component, for example, a sequence such as poly (A) and poly (T), an artificially synthesized polymer molecule, a nucleic acid prepared by a nucleic acid amplification technique (for example, PCR), a nucleic acid cloned into a vector, and the like. Methods for preparing these biopolymers 51 are well known in the relevant technical field, and those skilled in the art can appropriately select the preparation method according to a type of the biopolymer 51. In the present embodiment, the analysis of the biopolymer 51 refers to a characteristic analysis of the nucleic acid constituting the biopolymer 51. For example, the analysis of the biopolymer 51 refers to analysis of a sequence order of a nucleic acid monomer constituting the biopolymer 51 (sequencing), determination of a nucleic acid length, detection of a single nucleotide polymorphism, determination of the number of biopolymer, and detection of a conformation polymorphism (a copy number polymorphism, insertion, deletion, or the like) in a biopolymer.

Figure 17:
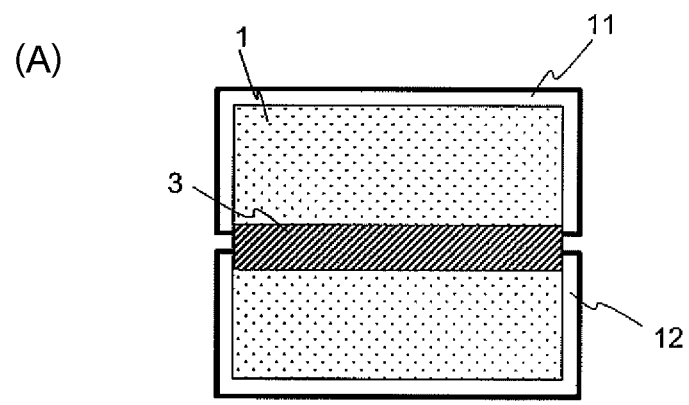
FIGS. 17(A)-17(C) are schematic views illustrating a method for measuring a biological molecule using a stored thin film device.
Figure 17:
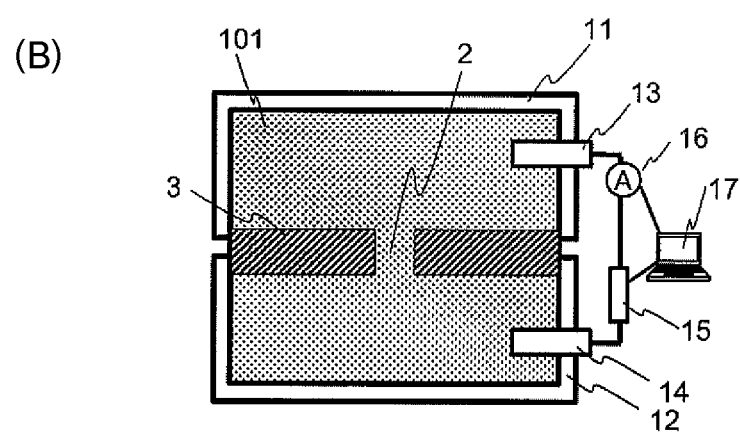
Figure 17:
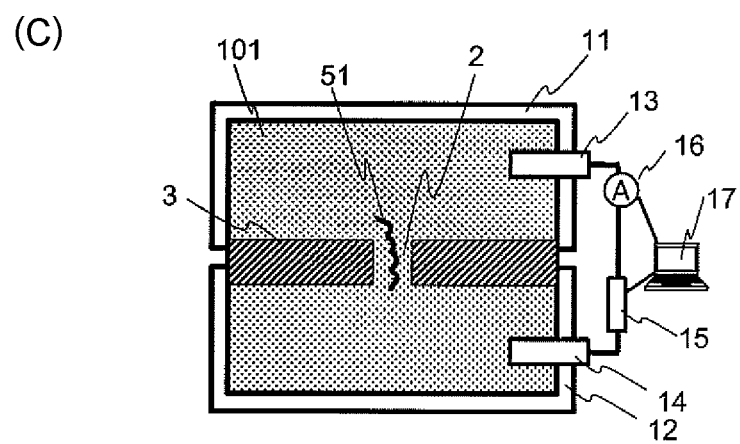

When the concentration of salt contained in the solution 1 is less than 1 mmol/L or the like so that it is difficult to obtain sufficient electrical conductivity to perform current measurement, it is necessary to replace the solution 1 with a solution 101 for current measurement as illustrated in FIG. 17. The solution 101 is preferably a solution containing a salt of 1 mmol/L or more to be used in general nanopore measurement. Further, it is desirable to increase the salt concentration such that the electrical conductivity increases in order to improve a signal during the current measurement, and the salt concentration is preferably 10 mmol/L or more, and more preferably 100 mmol/L or more. As a cation contained in the solution 101, ionizing cations can be used, and typically, it is preferable to use a Group I element or a Group II element such as Li, Na, K, Rb, Cs, Mg, Ca, Sr, and Ba. As an anion contained in the solution 101, ionizing anions can be used, and it is preferable to select the anion based on the compatibility with an electrode material. For example, when silver halide is used as the electrode material, it is preferable to use halide ions such as I, Br and Cl as the anion. Further, the anion may be organic anions represented by glutamate ion or the like. Note that the procedure illustrated in FIG. 16 has an advantage that fewer work processes are required as compared with the procedure illustrated in FIG. 17.

When a low-temperature solution is used as the solution 1, a voltage may be applied while keeping the apparatus for storing the thin film device at a low temperature when a nanopore is opened as illustrated in FIG. 16(B) or 17(B). When the pore is opened by applying the voltage while keeping the solution in the apparatus for storing the thin film device at a low temperature, a dielectric breakdown voltage of the thin film 3 can be increased, and it is possible to prevent soft breakdown that is likely to occur when the thin film with a low dielectric breakdown voltage is subjected to insulation breakdown and to stabilize a current characteristic. Further, when measuring the biopolymer 51 as illustrated in FIG. 16(C) or 17(c), the measurement may be performed while keeping the apparatus for storing the thin film device at a low temperature in the case of using the low-temperature solution for the solution 1. If DNA or the like is measured with the apparatus for storing the thin film device kept at a low temperature, the speed of DNA passing through the nanopore can be delayed.

One specific example of the measurement method described above is given as follows. First, the thin film having been subjected to hydrophilic treatment is incorporated into the first tank 11 and the second tank 12 of the container of the apparatus for storing the thin film device on the manufacturer side, and the inside of the solution tank is filled with a 1 mol/L KCl aqueous solution. At this time, the first electrode 13 and the second electrode 14 are provided in the first tank 11 and the second tank 12, respectively, and a state where the first electrode 13 is in contact with the solution in the first tank 11 and the second electrode 14 is in contact with the solution in the second tank 12 is formed. Further, the first electrode 13 and the second electrode 14 are short-circuited to have a potential difference of 0 V such that the thin film 3 does not deteriorate. Thereafter, the apparatus for storing the thin film device is delivered to the customer side for about a week by refrigerated transportation (cooled and maintained at +2° C. to +8° C. or the like). On the customer side, the delivered apparatus for storing a thin film device is stored in the refrigerator for two to three weeks or more (in the state of being cooled and maintained at about 4° C.), and the apparatus for storing the thin film device is taken out after finishing preparation of a biological sample as a measurement sample and is connected to the apparatus constituted by the power supply device 15, the ammeter 16, and the control and measurement device 17. Then, a high voltage is applied to the thin film 3 by the power supply device 15, the ammeter 16, and the control and measurement device 17, and the nanopore 2 is provided by dielectric breakdown. Finally, a biological sample 51 as the measurement sample is introduced, and the biological sample during passage through the nanopore 2 is measured and analyzed.

Hereinafter, an experimental example verifying the effect of the present embodiment is illustrated. In this experiment, a thin film device containing a SiN film was stored in the state of being immersed into solutions of various conditions such that the solution is in contact with both sides of the thin film. The thin film device was taken out of the solution after a lapse of a certain period of time and washed, and then, 1 mol/L $CaCl_2$ (room temperature) was filled above and below the thin film device. Then, a voltage was applied to the thin film to measure a dielectric breakdown voltage and a current value passing through the film.

Figure 18:
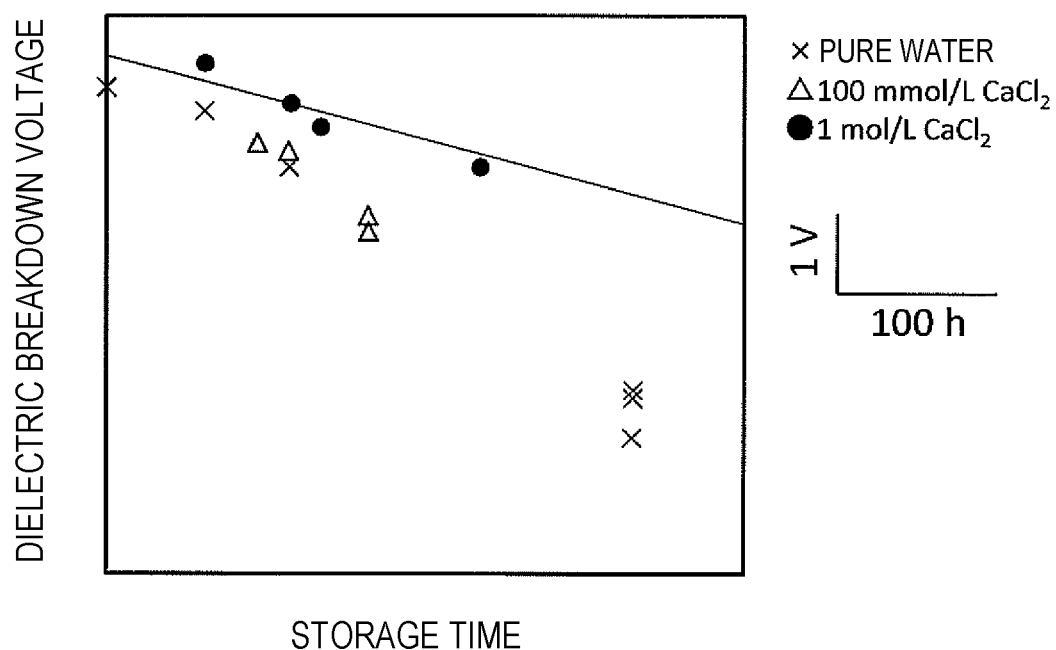
FIG. 18 is a view illustrating experimental results of changes over time in dielectric breakdown voltage.

First, it was verified that the SiN film was gradually etched so that the dielectric breakdown voltage decreased when the thin film device containing the SiN film was stored in an aqueous solution for a long time as described above. FIG. 18 illustrates changes over time in dielectric breakdown voltage when the thin film device was stored in aqueous solutions of pure water, 100 mmol/L $CaCl_2$, or 1 mol/L $CaCl_2$ (all temperatures were 25° C.). Based on these results, it has been found that a dielectric breakdown voltage V decreases linearly with respect to time t under any storage condition. In general, it is considered that a film thickness decreases almost linearly with respect to the immersion time in $H_2O$ since an etching rate in the depth direction of the thin film is constant. Further, dielectric breakdown strength of the thin film is V/nm, and the dielectric breakdown voltage is almost linear with respect to the film thickness. That is, the dielectric breakdown voltage decreases almost linearly with respect to the immersion time in $H_2O$. Therefore, the experimental result that the dielectric breakdown voltage decreases linearly with respect to the time, which is illustrated in FIG. 18, supports that the decrease of the dielectric breakdown voltage originates from etching with $H_2O$.

It can be understood that 1 mol/L $CaCl_2$ is effective in extension of a life since the decrease of the dielectric breakdown voltage is suppressed as compared with pure water and 100 mmol/L $CaCl_2$. It is considered that the extension of the life is caused since 1 mol/L $CaCl_2$ aqueous solution contains a high concentration of salt, and the salt hydrates with water to vary activation energy of a reaction that $H_2O$ etches the SiN film. The above results support the hypothesis that $H_2O$ etches the SiN film, and further, indicate that the solution containing a high concentration of salt (1 mol/L or more) can extend the life.

Figure 19:
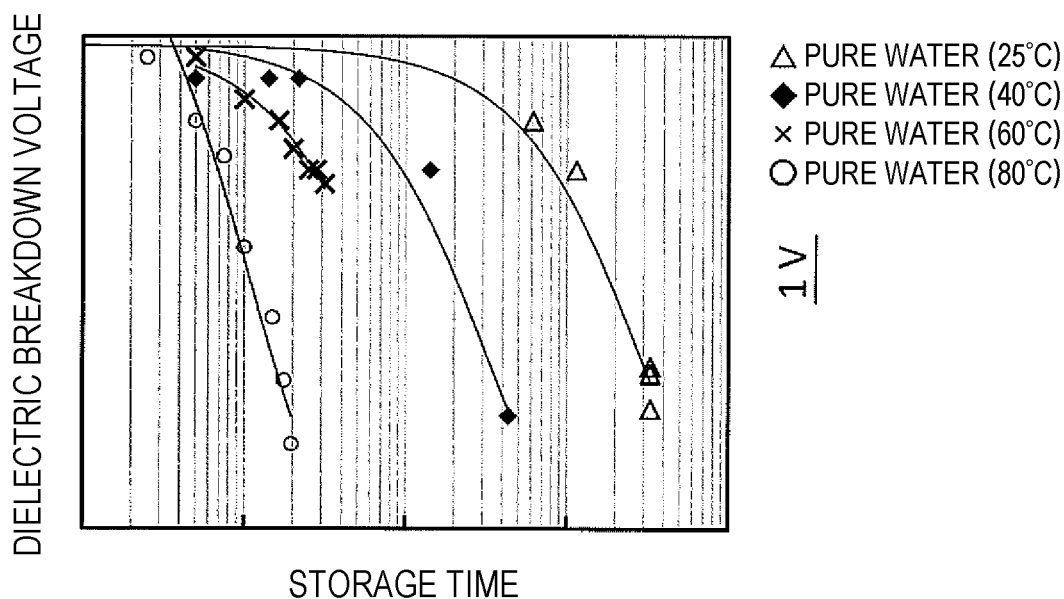
FIGS. 19(A)-19(B) are views illustrating experimental results of changes over time in dielectric breakdown voltage.
Figure 19:
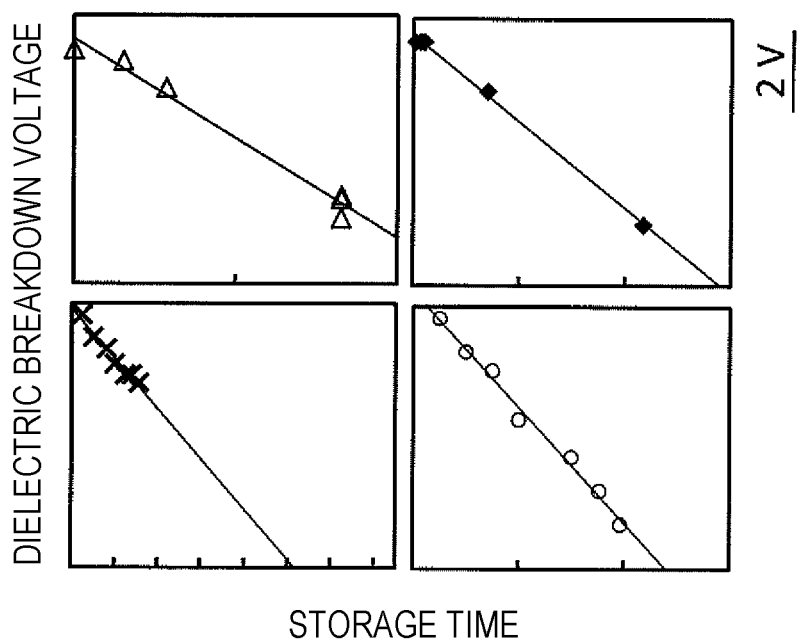

FIG. 19 illustrates changes over time in dielectric breakdown voltage when a thin film device was stored in pure water and a storage temperature was changed (25° C., 40° C., 60° C., and 80° C.). FIG. 19(A) is represented on the horizontal axis logarithmic scale, and FIG. 19(B) is represented on the horizontal axis linear scale. As apparent from FIG. 19(A), it is illustrated that the dielectric breakdown voltage decreases in a shorter period of time as the temperature during storage is higher. A straight line illustrated in FIG. 19(B) represents an approximate straight line during storage at each temperature, and it has been found that the dielectric breakdown voltage V decreases linearly with respect to a storage time t under any storage condition. This result is similar to the result of FIG. 18 and supports that the deterioration of the film originates from the etching by $H_2O$.

Figure 20:
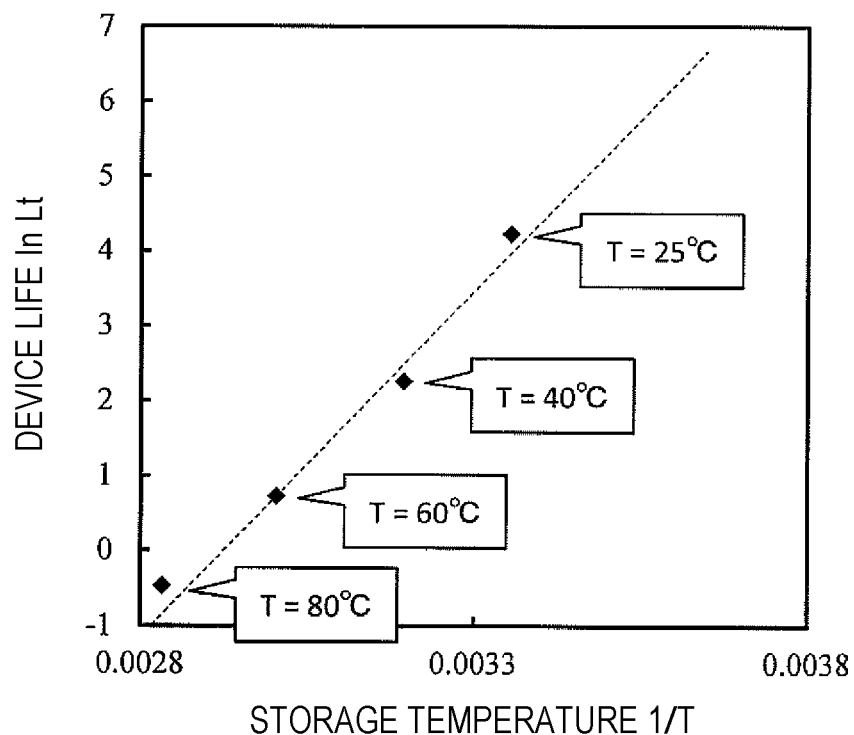
FIG. 20 is a view illustrating a relationship between a temperature and a device life.

Further, when a relationship between a time (device life) Lt until the dielectric breakdown voltage decreases by 1 V and the storage temperature T is summarized based on FIG. 19, the relationship in FIG. 20 is obtained. Black plots in FIG. 20 represent values obtained from experimental data in FIG. 19, and a dotted line represents an approximate straight line. The results in FIG. 20 represent that $\ln Lt \propto 1/T$, which suggests that the device life can be expressed by an Arrhenius-type relational expression. Activation energy E during storage in pure water can be calculated from a slope of the straight line.

Figure 21:
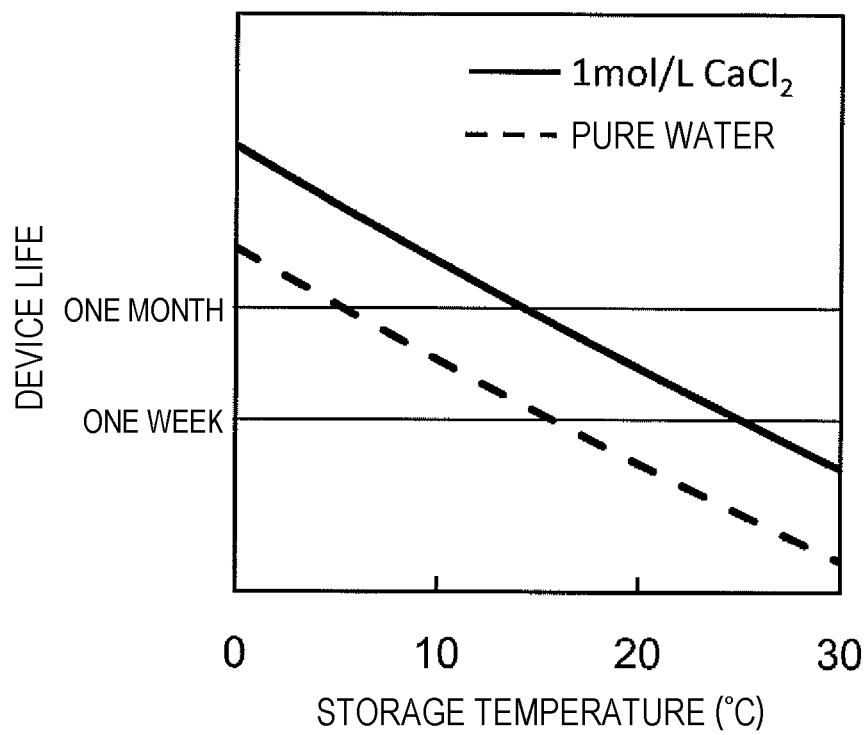
FIG. 21 is a view illustrating the relationship between the temperature and the device life.

FIG. 21 illustrates the Arrhenius relationship between the device life and the storage temperature when the thin film device was stored in pure water and a 1 mol/L $CaCl_2$ aqueous solution based on the previous experimental results. The results during storage in pure water illustrated in FIG. 21 are obtained by changing the vertical and horizontal axes of the approximate straight line illustrated in FIG. 20, and the device life Lt is represented on a vertical axis logarithmic scale, and the storage temperature T is illustrated on the horizontal axis. Subsequently, when calculating the results during storage in the 1 mol/L $CaCl_2$ aqueous solution illustrated in FIG. 21, first, the time (device life) Lt until the dielectric breakdown voltage decreases by 1 V during storage at 25° C. was calculated from the results of FIG. 18. As compared with the device life during storage in pure water while considering A and $[H_2O]^{-n}$ illustrated in (Formula 1) to be the same as those during storage in pure water, and activation energy during storage in the 1 mol/L $CaCl_2$ aqueous solution was calculated to obtain FIG. 21. It has been found based on FIG. 21 that a minimum storage temperature (cooling temperature) required to obtain an arbitrary device life can be read, and the device life of a week was obtained at a temperature lower than 15° C. in the pure water storage and at a temperature lower than 25° C. in the 1 mol/L $CaCl_2$ aqueous solution storage. Further, it has been found that the device life of a month was obtained at a temperature lower than 5° C. in the pure water storage and at a temperature lower than 15° C. in the 1 mol/L $CaCl_2$ aqueous solution storage.

Figure 22:
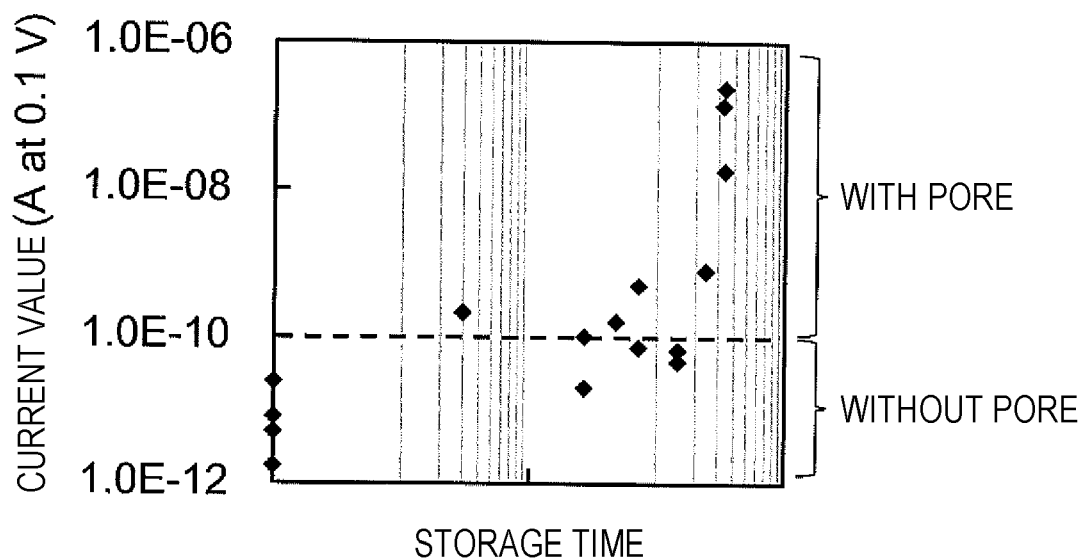
FIG. 22 is a view illustrating a relationship between a storage time and a leakage current.

FIG. 22 illustrates values of a current passing through the film when the thin film device was stored in pure water at 25° C. and a voltage of 0.1 V is applied. When the dielectric breakdown voltage decreases to 0.1 V or less with the storage in the aqueous solution, the dielectric breakdown occurs even when a low voltage such as 0.1 V is applied as in biological molecule measurement or the like. Further, a potential difference of 0.1 V or more may occur between electrolyte solutions filled above and below the thin film due to static electricity on the solution tank surface, and the film is also dielectrically broken with the influence of such static electricity. If a pore obtained by dielectric breakdown is present in the film, an ionic current of $1 \times 10^{-10}$ A or more is generated since the ionic current flows through the pore when 0.1 V is applied. Therefore, by examining whether the current value exceeds $1 \times 10^{-10}$ A, it is possible to determine whether the film has been dielectrically broken. As illustrated in FIG. 22, it is illustrated that the number of thin film devices exceeding $1 \times 10^{-10}$ A increased with a lapse of time, which represents that the dielectric breakdown voltage gradually decreased by etching with $H_2O$, and the dielectric breakdown is caused by static electricity or voltage when 0.1 V was applied. Even from this result, it has been confirmed the decrease of the dielectric breakdown voltage caused by the long-term storage in the aqueous solution.

Figure 23:
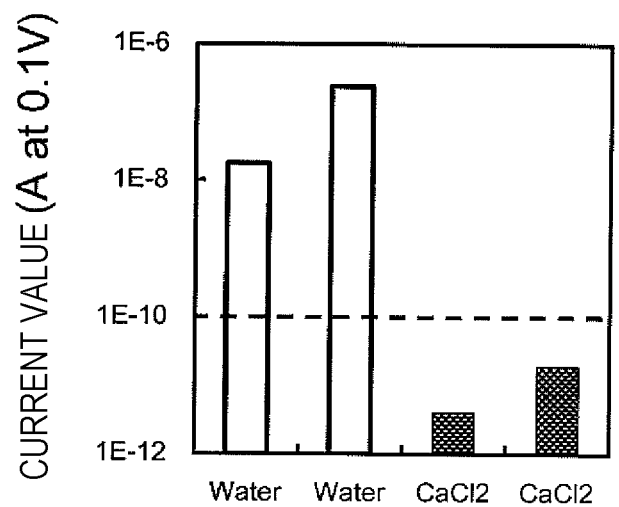
FIG. 23 is a view illustrating a leakage current under a solution condition having an effect of preventing deterioration.

FIG. 23 illustrates current values measured at the time of applying 0.1 V after storing thin film devices having the same film thickness in pure water at 25° C. and a 1 mol/L $CaCl_2$) solution at 25° C. for two weeks. As a result, a leakage current passing through a pore was observed in the pure water storage, but it was possible to suppress a leakage current in the 1 mol/L $CaCl_2$ storage. Even from this result, it has been confirmed that the life is extended by using 1 mol/L $CaCl_2$.

Figure 24:
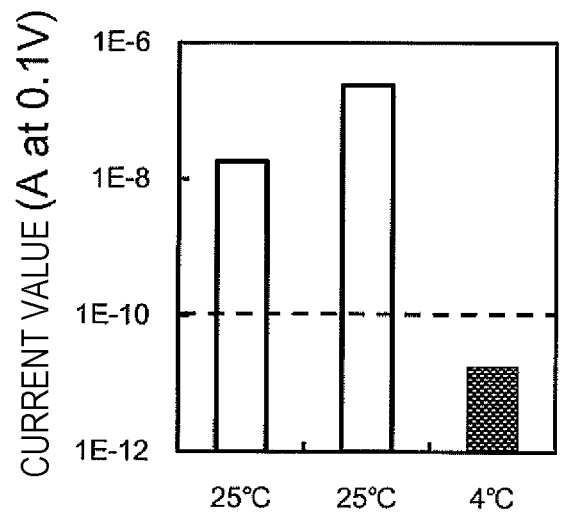
FIG. 24 is a view illustrating a leakage current under a solution condition having the effect of preventing deterioration.

FIG. 24 illustrates current values measured at the time of applying 0.1 V after storing thin film devices having the same thickness in pure water at 25° C. and 4° C. for two weeks. As a result, a leakage current passing through a pore was observed in the storage at 25° C., but it was possible to suppress a leakage current in the storage at 4° C. From this result, it has been confirmed that the life is extended by lowering the temperature during storage.

Figure 25:
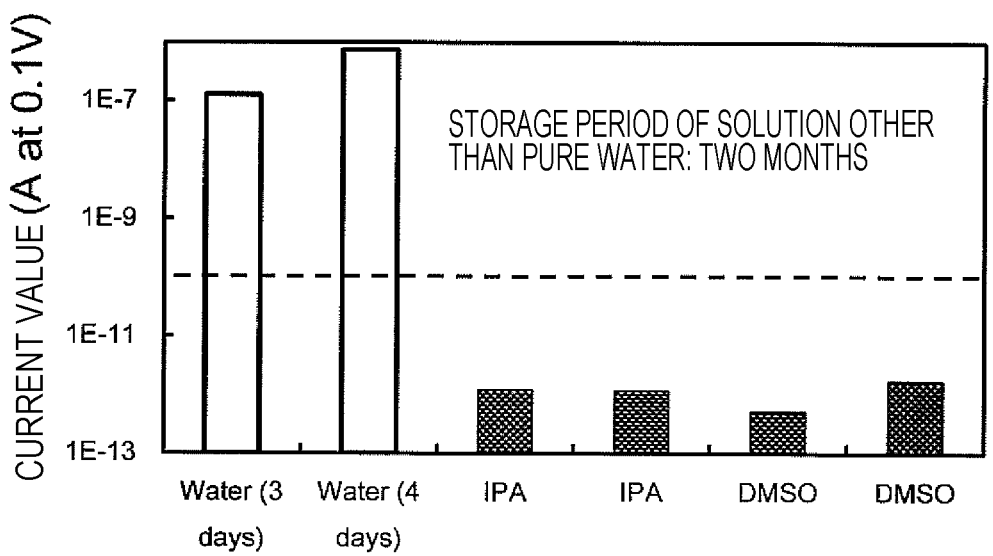
FIG. 25 is a view illustrating a leakage current under a solution condition having the effect of preventing deterioration.

FIG. 25 illustrates current values measured at the time of applying 0.1 V after storing thin film devices having the same thickness in pure water at 25° C. and organic solvents (IPA and DMSO) at 25° C. Storage days were differently set to three or four days for the pure water storage and two months for the organic solvent storage. As a result, a leakage current passing through the pore was observed in the pure water storage, but it was possible to suppress a leakage current in the organic solvent storage despite the long storage time. From this result, it has been confirmed that the life is extended by lowering the $H_2O$ concentration using the organic solvent as the solution during storage.

Although the experimental results obtained using the film containing Si (SiN film) were exemplified in the above experimental examples, it is a matter of course that the etching with $H_2O$ is not limited to the film containing Si. Even if a material of the film is graphene or the like, it is considered that graphene is oxidized with $H_2O$ to become graphene oxide and eventually is decomposed into $CO_2$ and the like, and thus, the present technique can be applied.

Incidentally, the invention is not limited to the above-described embodiments and includes various modifications. For example, the above-described embodiments have been described in detail in order to describe the present invention in an easily understandable manner, and are not necessarily limited to those including the entire configuration that has been described above. Further, some configurations of a certain embodiment can be substituted by configurations of another embodiment, and further, a configuration of another embodiment can be also added to a configuration of a certain embodiment. Further, addition, deletion, or substitution of other configurations can be made with respect to some configurations of each embodiment.

REFERENCE SIGNS LIST

1 solution
2 nanopore
3 thin film
4 support structure
11 first tank
12 second tank
13 first electrode
14 second electrode
15 power supply device
16 ammeter
17 control and measurement device
31 introduction and discharge ports
32 sealing structure
41 temperature adjustment mechanism
51 biopolymer

The invention claimed is:

1. A method for storing a thin film device having an insulating thin film containing Si and having a maximum thickness of 100 nm, the method comprising:
a step of hydrophilizing the thin film device; and
a step of storing the hydrophilized thin film device in contact with a solution in a container having a tank that is sealed for prevention of volatilization and that satisfies any of conditions (1) to (3):
(1) a solution containing water in a volume ratio in a range from 0% to 30%;
(2) a solution cooled and maintained at a temperature higher than its solidification point and lower than 15° C.; and
(3) a solution that contains a salt with a concentration of 10 mol/L or more and a saturation concentration or less and is cooled and maintained to a temperature higher than its solidification point and lower than 25° C.

2. The method for storing the thin film device according to claim 1, wherein the solution is a solution that satisfies any of following conditions (4) to (6):
(4) a solution containing water in a volume ratio in a range from 0% to 5%;
(5) a solution cooled and maintained at a temperature higher than its solidification point and lower than 5° C.; and
(6) a solution containing a salt with a concentration of 1 mol/L or more and a saturation concentration or less, the solution cooled and maintained to a temperature higher than its solidification point and lower than 15° C.

3. The method for storing the thin film device according to claim 1, wherein the solution satisfies the condition (3), and the solution contains the salt with the concentration of 100 mol/L or more.

4. The method for storing the thin film device according to claim 1, wherein the solution is a solution that satisfies following condition (4):
(4) a solution containing water in a volume ratio in a range from 0% to 5%.

5. The method for storing the thin film device according to claim 1, wherein the solution satisfies the condition (1).

6. The method for storing the thin film device according to claim 1, wherein the solution satisfies the condition (2).

* * * * *